United States Patent [19]

Rodland et al.

[11] Patent Number: 4,647,529

[45] Date of Patent: Mar. 3, 1987

[54] HYBRIDIZATION METHOD OF DETECTING NUCLEIC ACID SEQUENCES WITH PROBE CONTAINING THIONUCLEOTIDE

[76] Inventor: Karin D. Rodland, 3330 NE. 138th Pl., Portland, Oreg. 97230; Peter J. Russell, 8000 S.E. 35th, Portland, Oreg. 97202

[21] Appl. No.: 616,286

[22] Filed: Jun. 1, 1984

[51] Int. Cl.$^4$ .............. C12Q 1/68; C12P 19/56; G01N 33/566; C07H 15/12

[52] U.S. Cl. ........................... 435/6; 435/78; 436/501; 536/27

[58] Field of Search .............. 435/6, 78; 536/27; 436/501

[56] References Cited

U.S. PATENT DOCUMENTS

| | | | |
|---|---|---|---|
| 4,287,345 | 9/1981 | Kotani et al. | 546/261 |
| 4,302,204 | 11/1981 | Wahl et al. | 23/230.3 |
| 4,358,535 | 11/1982 | Falkow et al. | 435/34 |
| 4,399,216 | 8/1983 | Axel et al. | 435/6 |
| 4,446,237 | 5/1984 | Berninger | 435/6 |
| 4,455,370 | 6/1984 | Bartelsman et al. | 435/78 |
| 4,521,509 | 6/1985 | Benkovic et al. | 435/6 |
| 4,599,303 | 7/1986 | Yabusaki et al. | 435/6 |

FOREIGN PATENT DOCUMENTS

0123513 10/1984 European Pat. Off.

OTHER PUBLICATIONS

Miura, K. et. al., Preparation of $^{35}$S-Labeled . . . Chem. Pharm. Bull. 1982 30(3), pp. 1069–1072.
Chemical Abstracts I: 99:35603v (1983).
Chemical Abstracts II: 97:195359g (1982).
Freifelder, D., Molecular Biology: A Comprehensive Introduction to Prokaryotes and Eukaryotes, Science Books Int. (1983), pp. 414–425, 392.
Abstract of "Comparisons Using Sulfur-35 and Phosphorus-32 Labeled DNA for Hybridization on Nitrocellulose Filters," Radford, A. J., Anal. Biochem. 1983.
Rodland and Russell, Current Genetics 7:379 (1983).
Rodland and Russell, Abstract No. 1148, Federation Processings 42(7):1954 (1983).
Radford, Analytical Biochemistry, 134:269 (1983).
Singer and Ward, Proc. Natl. Acad. Sci. U.S.A. 79:7331 (1982).
Green and Rittenback, Gene Screen Hybridization Transfer Membrane Instruction Manual (1982), New England Nuclear (Boston, Mass.).
Vincent et al., "Preparation of DNA Labeled with High Specific Activity [$^{35}$S]–Deoxyadenosin 5'–[α–Thio] Triphosphate; the Use of $^{35}$S-Labeled Nucleic Acids as Molecular Hybridization Probes", New England Nuclear Technical Bulletin (1982).
Langer, Waldrop and Ward, Proc. Natl. Acad. Sci. U.S.A. 78:6633 (1981).
Kunkel et al., PNAS USA 78:6734 (1981).
Putney et al., PNAS USA 78:7350–7354 (1981).
Wahl, Stern and Stark, Proc. Natl. Acad. Sci. U.S.A. 76:3683 (1979).
Vosberg and Eckstein, Biochemistry 16:3633 (1977).
Alwine et al., PNAS USA 74:5350 (1977).
Rigby et al., J. Mol. Biol. 113:237 (1977).
Strothkamp and Lippard, Proc. Natl. Acad. Sci. U.S.A. 73:2536 (1976).
Southern, J. Mol. Biol. 98:503 (1975).
Rodland and Russell, New England Nuclear Technical Bulletin, New Product News, vol. 1, No. 9 (Sep. 1983).
Rodland and Russell, poster presentation, "Effect of Deoxycytidine 5'–[αThio]Triphosphate–[$^{35}$S] on the Reassociation Kinetics and S$_1$ Nuclease Sensitivity of Plasmid DNA", (presented Jun. 7, 1983).

Primary Examiner—Sidney Marantz
Assistant Examiner—L. Krawczewicz
Attorney, Agent, or Firm—Klarquist, Sparkman, Campbell, Leigh & Whinston

[57] ABSTRACT

Improved hybridization probe compositions and method for detecting nucleic acids are provided. A hybridization probe constructed to contain thionucleotides is hybridized to a nucleotide sequence of interest in the absence of formamide, DTT and dextran sulfate. If a cold ($^{32}$S) thionucleotide is incorporated into the probe molecule, the probe is provided with a detectable label, radioactive or otherwise.

45 Claims, No Drawings

HYBRIDIZATION METHOD OF DETECTING NUCLEIC ACID SEQUENCES WITH PROBE CONTAINING THIONUCLEOTIDE

BACKGROUND OF THE INVENTION

1. Field of the Invention

Recent advances in the general field of molecular biology have made it possible to detect specific genes of clinical and commercial importance. For example, the structures of various genes and gene sequences associated with specific human diseases are known, as are various techniques for detecting the presence of such genes. It is therefore possible to diagnose human disease at the genetic level.

The most common technique for detecting a particular gene sequence is hybridization. A particular nucleotide sequence or "probe" is marked with a detectable label, typically a radioactive label or chemical modification, and combined with the nucleic acid sample of interest, either in situ as part of intact cells or as isolated DNA or RNA fragements. The sample can be either free in solution or immobilized on a solid substrate. If the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred and for measuring the amount of DNA/RNA sample present. The hybridization technique is of prime importance in basic research directed at understanding the relationship between nucleotide sequences and their function, as well as in diagnostic use to detect known aberrant genes or disease agents such as viruses or bacteria.

The main limitation of present gene detecting methods is that they are not sensitive enough and therefore require a relatively large amount of sample to accurately verify the existence of a particular gene sequence. This is not surprising since the detection of a single gene in the entire genetic repertoire of a human being requires locating one part in one to ten million. In fact, most hybridization methods require at least one in ten micrograms of purified DNA, representing a substantial sample of cells, to perform a reliable analysis. This limitation is particularly significant in pre-natal diagnosis of genetic disorders where only a small cell sample can be taken or to identify infectious agents such as viruses in small tissue samples. Consequently, there is a substantial interest in developing gene detecting methods which will increase the sensitivity of the hybridization assay without sacrificing its specificity.

DESCRIPTION OF THE PRIOR ART

The hybridization procedure typically includes the initial steps of isolating the DNA sample of interest and purifying it chemically. The DNA sample is then cut into pieces with an appropriate restriction enzyme. The pieces are separated by size through electrophoresis in a gel, usually agarose or acrylamide. The pieces of interest are transferred to an immobilizing membrane in a manner that retains the geometry of the pieces. The membrane is then dried and prehybridized to equilibrate it for later immersion in a hybridization solution.

A probe labeled with a radioactive isotope is constructed from a nucleotide sequence complementary to the DNA sample by a conventional nick translation reaction, using a DNase and DNA polymerase, although other types of labels can be used. The probe and sample are then combined in a hybridization buffer solution and held at an appropriate temperature until annealing occurs. Thereafter, the membrane is washed free of extraneous materials, leaving the sample and bound probe molecules supported on the membrane. The signal of the bound probe molecules is detected and quantified by autoradiography and/or liquid scintillation counting.

Southern, *J. Mol. Biol.* 98: 503 (1975) teaches the transfer of DNA fragments to strips of nitrocellulose after the fragments have been resolved by electrophoresis in agarose gels. Immobilization of DNA on diazobenzyloxymethyl cellulose is taught by Noyes and Stark, *Cell* 5: 301 (1975). Alwine et al., *PNAS USA* 74: 5350 (1977) teach a method for detecting specific RNA molecules that are resolved in agarose gels, transferred to diazobenzyloxymethyl paper and then hybridized with DNA probes. Similarly, Reiser et al., *Biochem. Biophys. Res. Comm.* 85: 1104 (1978), teach the detection of small DNA fragments resolved in polyacrylamide gels by immobilizing the same on diazobenzyloxymethyl paper and then hybridizing them to DNA probes.

Both Bittner et al., *Anal. Biochem.* 102: 459 (1980) and Stellwag and Dahlberg, *Nucl. Acid Res.* 8: 299 (1980) teach the use of an electrical current to transfer DNA and RNA fragments from either agarose or acrylamide gels to diazobenzyloxymethyl paper. Similarly, electrophoretic transfer of nucleic acids to diazophenylthioether paper is taught by Reiser and Wardale, *Eur. J. Biochem.* 114: 569 (1981).

A New England Nuclear (Boston, Mass.) technical bulletin entitled "Gene Screen Hybridization Transfer Membrane Instruction Manual", by D. J. Green and D. R. Rittenbach (1982) teaches a modification of two different techniques ("electrophoretic transfer" and "capillary wicking") for immobilizing DNA and RNA samples on a porous substrate, specifically nylon-base membranes.

Nucleic acid probes have heretofore been labeled separately with either tritium or radioactive phosphorus [$^{32}$P] by nick translation, Rigby et al., *J. Mol. Biol.* 113: 237 (1977) or with biotinylated uridine, Narayanswami, Hutchison and Ward, *J. Cell Biol.* 95: 74a (1982). Other references, besides Rigby et al., identifying radioactive labels for DNA probes include Wahl et al., U.S. Pat. No. 4,302,204 ($^{32}$P); Falkow et al., U.S. Pat. No. 4,358,535 ($^{32}$P, $^3$H, $^{14}$C); and Axel, et al., U.S. Pat. No. 4,399,216 ($^{32}$P). A New England Nuclear technical bulletin, Vincent et al., "Preparation of DNA Labeled With High Specific Activity [$^{35}$S]-Deoxyadenosine 5'-[α-Thio]Triphosphate; the Use of $^{35}$S-Labeled Nucleic Acids as Molecular Hybridization Probes" (1982) teaches that a hybridization probe labeled with [$^{35}$S]-deoxyadenosine 5' [α-thio]triphosphate is qualitatively indistinguishable from a conventional $^{32}$P labeled probe.

Wahl et al., U.S. Pat. No. 4,302,204 teach the use of ionic polymers, particularly dextran sulfate, to increase the local concentration of nucleic acids in hybridization reactions and in turn increase the signal of the DNA sample of interest. It also describes the use of a depurination step to increase the efficiency with which very large nucleic acid segments are transferred from a gel to a solid membrane.

A method of incorporating a phosphorothioate analog of deoxynucleotides, namely $^{32}$S, into DNA polymers, using known DNA polymerases (*E. coli* DNA polymerase I and *E. coli* DNA polymerase III) is described by Kunkel et al., *PNAS USA* 78: 6734 (1981). This reference mentions the use of thionucleotides to induce site-specific mutations as an application of the method. Putney et al., *PNAS USA* 78: 7350–7354 (1981) teach that a protective effect against enzymatic degradation occurs following the incorporation of a thionucleotide ($^{32}S$) into DNA polymers.

The use of a polyfunctional disulfide compound to cross-link protein molecules is taught by Kotani et al., U.S. Pat. No. 4,287,345.

The present invention improves prior methods of detecting DNA genes and gene sequences by amplifying the detectable signal generated by bound probe molecules, thereby providing an accurate and reliable method for detecting and quantifying particular nucleotide sequences, even in relatively small samples. Accordingly, the present invention includes as its objects the following:

(1) to increase the mass of complementary DNA bound to specific gene sequences immobilized on a membrane;
(2) to increase the signal-to-noise ratio produced in hybridization reactions involving immobilized DNA;
(3) to improve the resolution of bands visualized by autoradiography of radioisotopically-labeled DNA;
(4) to produce radioisotopic probes which will provide the same intensity of autoradiographic signal as obtained with $^{32}P$-labeled probes, but with less danger of radiation exposure to the worker due to the decreased emission energy of the probe;
(5) to improve existing protocols for hybridizations, especially filter hybridizations, with $^{35}S$-labeled probes and reduce both the direct cost of the reaction mixture and the labor cost of the procedure; and
(6) to produce a system of signal amplification which is not dependent upon the use of radioisotopes and which is compatible with a variety of probe-labeling systems.

Other objects will be apparent from the Description of a Specific Embodiment.

SUMMARY OF THE INVENTION

In accordance with the foregoing objects, the present invention comprises a hybridization probe and method for detecting nucleotide sequences. Initially, a DNA sample of interest is purified chemically and cut into pieces with a suitable restriction enzyme. The pieces are separated by size by electrophoresis in a suitable gel. The pieces of interest are then transferred to an immobilizing medium, such as a nitrocellulose or nylon-base membrane, that retains the geometry of the pieces. The membrane is thereafter dried and prehybridized to equilibrate it for later immersion in a hybridization solution.

A probe is constructed from a nucleotide sequence complementary to the gene sample by a nick translation reaction, using both a DNase and DNA polymerase. In this reaction, a thionucleotide containing either $^{32}S$ or $^{35}S$, is incorporated into the probe molecule. If non-radioisotopic sulfur, i.e., $^{32}S$, is incorporated into the probe molecule, the molecule is also labeled with a radioisotope, such as $^{32}P$, $^{3}H$, $^{14}C$, $^{35}S$, or $^{125}I$, or some other detectable marker, radioactive or otherwise. The probe and sample are thereafter combined in a hybridization buffer and incubated. In such buffer, the probe and sample are combined in the absence of reducing agents, nonpolar solvents and dextran sulfate. After a specified incubation period, the membrane is removed from the buffer and washed free of extraneous materials. The presence or absence of the particular nucleotide sequence is detected by autoradiography and quantified by liquid scintillation counting.

DESCRIPTION OF THE SPECIFIC EMBODIMENTS

The following definitions are provided for ease in understanding the description:

thionucleotides—phosphorothioate analogs of the deoxynucleotides normally found in DNA polymers, in which a sulfur molecule has been substituted for one of the oxygen molecules in the alpha-phosphate group. A specific example is deoxycytosine-5′α-thiotriphosphate:

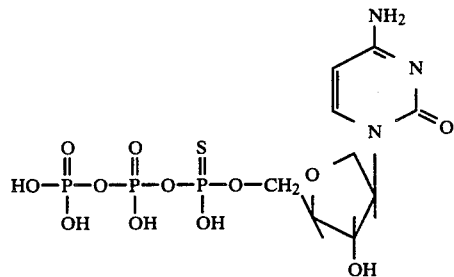

hybridization—the annealing of two complementary, single-stranded DNA molecules, particularly when the individual strands come from separate sources. The annealing is specific for complementary base pairs, and therefore reproduces the genetic code of the specific gene hybridized;

nick translation—a method for incorporating specific nucleotides into a DNA polymer by using the enzyme DNase to remove bases from the polymer (nicking) and the enzyme DNA polymerase (e.g., *E. coli* DNA polymerase I) to repair these nicks by incorporating nucleotide triphosphates into the DNA polymer. If the nucleotide triphosphates contain an identifiable marker, such as a radioisotopic molecule or a chemically modified base, the entire DNA polymer can be identified by detecting the marker;

hybridization membrane—a solid yet porous medium which will bind nucleic acid polymers but not free nucleotides in a non-covalent manner.

The most common hybridization membranes are composed of either nitrocellulose or a surface-modified nylon;

liquid scintillation counting—a method of detecting radioactivity by detecting light emitted as a result of radioactive decay within a special chemical "fluor"; and autoradiography—a method of detecting radioactivity by exposing x-ray film to the particles of radioactive decay.

The subject invention involves four basic steps. Initially, a DNA probe molecule complementary to a nucleic acid sample of interest is constructed to have thionucleotides incorporated throughout its length and a bound detectable marker. The nucleic acid sample is immobilized on a solid hybridization membrane. The order in which these two steps are carried out is not important. The probe is then hybridized to the immobilized DNA sample under specified reaction conditions.

Finally, the signal generated by probe molecules hybridized to the nucleic acid sample is detected and quantified.

CONSTRUCTION OF THE PROBE MOLECULE

A preselected thionucleotide containing either $^{32}S$ or $^{35}S$ as the thiol group, is incorporated into DNA polymers complementary to the nucleotide sequence of interest. The resulting hybridization probe has the formula

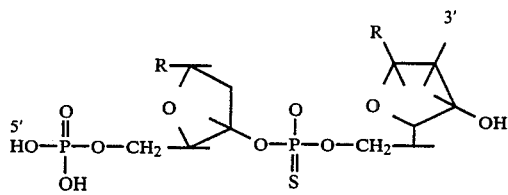

wherein R is any purine or pyrimidine base and S is either $^{32}S$ or $^{35}S$. The thionucleotides are incorporated using the basic nick translation technique taught by Rigby et al., *J. Mol. Biol.* 113: 237 (1977). More specifically, a piece of cloned DNA known to contain the coding sequence of the gene sample of interest is incubated under proper ionic conditions in a mixture containing two enzymes, DNase I and *E. coli* DNA polymerase I, and the preselected thionucleotides, as well as the other necessary deoxynucleotides. The DNase enzyme removes individual nucleotides from the DNA polymers. The resulting gaps or "nicks" are then repaired by the DNA polymerase I enzyme which facilitates the linear incorporation of the nucleotides thionucleotides into the DNA polymers to fill the nicks.

The thionucleotides are incorporated in accordance with the reaction conditions described in the New England Nuclear technical bulletin, Vincent et al., (1982), supra, with one modification. This technical bulletin teaches that the mixture should be incubated at 14° C. for at least 90 minutes, with a graph showing the optimum incubation period to be about 8 to 24 hours for $^{35}S$ labeled DNA. It has been determined, however, that the optimum incubation for the thiol group is at 14°-15° C. for about 5 to 6 hours, at which time about 0.1 to 1.0 pmoles of thionucleotide have been incorporated into each μg of DNA (0.03 to 0.3 ppt).

To terminate the nick translation reaction, one of several known methods may be used. One method involves separating the large thionucleotide-containing DNA polymers from the unincorporated thionucleotides by adding 2.5 volumes of ice-cold absolute ethanol and precipitating the mixture at a temperature of about −70° C. for about 20–30 minutes or overnight at about −20 C.°. The precipitated DNA is then collected by centrifugation in a tabletop microcentrifuge for about 10 minutes. Thereafter, the ethanol and dissolved nucleotides are discarded and the DNA polymer precipitate is re-suspended in an appropriate volume (100 ul per μg) of low ionic strength buffer consisting of a solution containing 10 mM Tris HCl, pH 7.5 (Sigma Chemical Co., St. Louis, Mo.), 10 mM $MgCl_2$ and 10 mM dithiothreitol.

By way of example, when the foregoing nick translation reaction is used to radioactively label the nucleic acid probes with thionucleotides containing deoxycytosine 5'αthio-triphosphateα-[$^{35}S$] (with a specific activity of 800–1300 Ci/mmole), the probe molecules have a specific activity of $1-20\times10^6$ dpm per μg DNA. Alternatively, if non-radioactive thionucleotides, such as deoxycytosine 5'αthio-triphosphateα[$^{32}S$] or deoxyadenosine 5'αthio-triphosphateα-[$^{32}S$] are incorporated into the nucleic acid probes, some other detectable marker such as a radioactive label must also be incorporated. Possible radioactive labels include $^{32}P$-labeled or $^3H$-labeled deoxyadenosine triphosphate, in which case the specific activity of the probe molecules would be comparable to those obtained with $^3H$-labeled or $^{32}P$-labeled probes lacking thionucleotides. By way of example, a radioactively-labeled probe with a deoxycytosine base has the formula

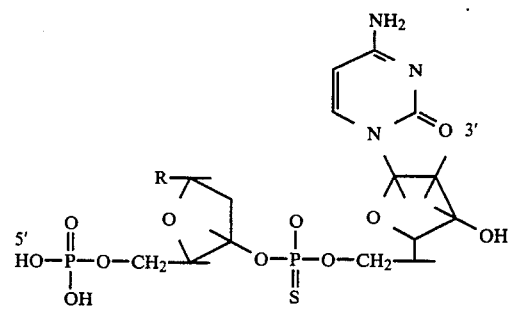

wherein R is any purine or pyrimidine base and the radioactive label is $^3H$ substituting for any H, $^{14}C$ substituting for any C, $^{32}P$ substituting for any P, $^{35}S$ substituting for the alpha thiol group in any thionucleotide or $^{125}I$ present in any iodinated modification to a purine or pyrimidine base.

The foregoing procedure can also be used with other labeling methods by which the nucleic acid probe is tagged with a non-radioactive, detectable marker, or in conjunction with such methods, since all nucleotide triphosphates present in the reaction mixture, including thionucleotide analogs, normal nucleotides containing a radioisotopic marker or chemically modified nucleotides, such as the biotinylated nucleotides described by Narayanswami, et al., supra, will be incorporated into the DNA sample. Thus, for example, $^{32}S$ and a biotinylated nucleotide such as biotinylated uridine can both be incorporated into the probe molecule, with the resulting formula

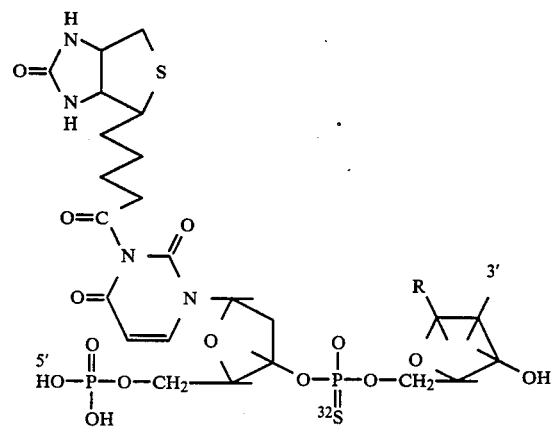

wherein R is any purine or pyrimidine base.

As a further example, the probe can be constructed with two detectable labels, a radioactive thionucleotide such as $^{35}S$ and a chemically modified nucleotide, with the resulting formula

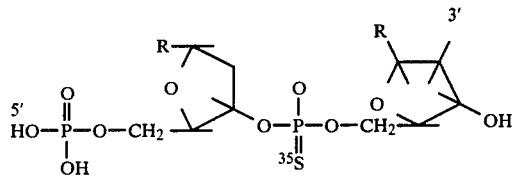

wherein R is any purine or pyrimidine base containing a detectable chemical modification and the radioactive label is $^3H$ substituting for any H, $^{14}C$ substituting for any C, $^{32}P$ substituting for any P, $^{35}S$ substituting for the alpha thiol group in any thionucleotide or $^{125}I$ present in any iodinated modification to any purine or pyrimidine base.

A second example of a detectable chemical modification is a chemiluminescent modification.

IMMOBILIZATION OF THE NUCLEIC ACID SAMPLE

The nucleic acid sample is conventionally treated to suspend the specific DNA fragments of interest in an agarose or polyacrylamide gel. The DNA fragments are treated with an alkali in a known manner to denature the double helix into two separate strands. For example, this can be accomplished by incubating the gel at room temperature for about 45-60 minutes in 0.5N NaOH, 1.5M NaCl, with gentle agitation. The gel is returned to a neutral pH by treating it with a neutralizing buffer (i.e., 1M Tris HCl, pH 6.5-7.5, 1.5M NaCl) for about 45-60 minutes at room temperature.

The denatured nucleic acid sample is thereafter immobilized on a hybridization membrane, typically using one of two techniques. One technique involves capillary wicking by a high-salt solution to transfer the DNA fragments from the gel, usually an agarose gel, to the hybridization membrane. The hybridization membrane, pre-equilibrated in distilled water, is placed directly on the gel, and a sandwich is constructed. A bridge is then formed between two reservoirs of wicking buffer (such as 1.5M NaCl, 0.15M sodium citrate). A wick of chromatography paper (Whatman 3M) is laid over the bridge, extending into the reservoirs. The gel/membrane sandwich is placed on the wick, with a stack of absorbent paper pads or towels placed on top of the membrane. Capillary transfers generally require about 16-24 hours of continuous wicking for optimum results, although any transfer time between 8 and 48 hours can be used successfully.

The capillary wicking technique was initially described by Southern, *J. Mol. Biol.* 98: 503 (1975) for use with nitrocellulose membranes. More recently, the technique has been used with nylon-base membranes such as "GeneScreen" and "GeneScreen Plus" introduced by New England Nuclear and other nylon membranes, including those manufactured by Pall Biodyne and Bio-Rad/AMFQ ("Zeta-Probe"). The published protocols for these nylon membranes are similar to those used with nitrocellulose membranes, although the recommended wicking buffer generally has one quarter to one half the ionic strength of the wicking buffer recommended by Southern.

The present invention works with any of the foregoing membranes, using the protocols recommended by the manufacturer, and should work with any other membranes having comparable characteristics. However, the best results are obtained with the "GeneScreen Plus" membrane, the protocol for which is described above. The foregoing procedure works with nylon membranes, regardless of whether the membrane is heated after the transfer is completed. However, with nitrocellulose membranes, the nucleic acid sample must be baked onto the membrane, preferably at 80° C. for about 2 hours, in a vacuum.

Alternatively, the nucleic acid sample may be immobilized on a nylon hybridization membrane using a technique known as "electrophoretic transfer" or "electroblotting". This technique involves the use of an electric current as the driving force to transfer the nucleic acid fragments from either an agarose or polyacrylamide gel to the membrane. The membrane, pre-equilibrated in distilled water or an appropriate buffer, is placed directly on the gel which has been treated as previously described to denature the DNA double helix, and a sandwich is constructed.

More specifically, the gel/membrane sandwich is placed in a holder especially adapted for use with an electrophoretic transfer apparatus, such as the "Trans-Blot" apparatus manufactured by Bio-Rad. The sandwich is surrounded with an appropriate buffer, such as 25 mM sodium phosphate, or a buffer containing 10 mM Tris, pH 7.8, 5 mM sodium acetate, and 0.5 mM EDTA (ethylenediaminetraacteic acid). A current of 600-800 mA is applied across the sandwich, which is positioned so that the membrane is between the gel and the anode. The DNA fragments are completely transferred to the membrane within 4-6 hours under these conditions. Overnight transfers of 14-16 hours using less current (<250 mA) are also feasible.

This technique was originally described by Stellwag and Dahlberg, *Nucleic Acids Res.* 8: 299 (1980) and Bittner et al., *Anal. Biochem.* 102: 459 (1980). Modifications of the foregoing protocol optimized for the various commercially available nylon membranes are published in the technical bulletins which accompany such membranes. The published protocols for both the "GeneScreen Plus" (New England Nuclear) and "Zeta-Probe" (Bio-Rad) membranes work well with this invention.

Yet another method of immobilizing the nucleic acid sample on a membrane, known as "dot blotting", is described more particularly in the Experimental Materials and Methods section. This technique is particularly suited for "field use" in that an entire tissue sample is immobilized on the membrane without preliminary isolation of the particular nucleotide sequence of interest.

It is believed that the present invention works best with membranes having the following characteristics: nylon instead of nitrocellulose base; charge modified instead of neutral surface; and large pore size (greater than 0.45 microns). Low salt treatment of the membrane during equilibration is also favored.

HYBRIDIZATION OF IMMOBILIZED DNA

After the DNA sample has been transferred to the membrane, by whatever method, the gel/membrane sandwich is disassembled and any contaminating gel is gently removed from the membrane by rubbing it with the transfer buffer. The membrane is then air-dried if nylon, or baked for about 2 hours at about 80° C. in vacuo if nitrocellulose, to strengthen the binding to the membrane. The membrane is then pre-equilibrated by incubating it at about 65° C. for about 12-24 hours in a pre-hybridization buffer typically containing 0.75M NaCl, 75 mM sodium phosphate, 5 mM EDTA, and 0.1% (w/v) sodium dodecyl sulfonate (SDS).

To initiate the hybridization reaction, $1-3\times10^6$ cpm of radioactively-labeled probe (<0.5 μg) is added to a heat-resistant plastic bag containing the hybridization membrane and about 1 ml of the pre-hybridization buffer for each 50 cm$^2$ of membrane. The labeled probe is distributed throughout the bag by gentle mixing. The bag is heat-sealed, and then incubated with constant agitation for about 4-30 hours, preferably about 20 hours, at about 65° C. The hybridization reaction is carried out in the absence of nonpolar solvents such as formamide, reducing agents such as dithiothreitol and 2-mercaptoethanol, and volume exclusion agents such as dextran sulfate.

After hybridization has proceeded for the desired time interval, the radioactive probe solution is removed and treated as radioactive waste (a step obviously unnecessary if a non-radioactive labeling system is used). Non-specifically bound probe molecules are removed by a washing procedure, such as that described by Jeffreys and Flavell, *Cell* 12:429 (1977). The simplest method includes six changes of a washing solution containing 0.3M NaCl, 30 mM sodium phosphate (pH 7.4), 2 mM EDTA and 0.1% SDS. In each wash cycle the solution is incubated for about ten minutes at about 65° C. with constant agitation. An additional stringent wash in 15 mM NaCl, 1.5 mM sodium phosphate, 0.1 mM EDTA, 0.1% SDS for about 30 minutes at about 42° C. is preferred, but is not essential to obtain low backgrounds.

Other *aqueous* formulations can be used with this invention, particularly those in which sodium citrate is substituted for sodium phosphate. The addition of certain additives, such as bovine serum albumin, polyvinyl pyrrolidone, Ficoll TM (molecular weight 400), oligoribonucleotides or denatured carrier DNA is also permissible. The temperature of the hybridization reaction is not critical within a broad range determined by the base composition of the DNA sample, although temperatures between 48° C. and 70° C. are generally used.

As further explained below, the phenomenon of increased binding is not observed if the hybridization is conducted at 37° C. in 50% formamide. Also, the presence of either dithiothreitol or 2-mercaptoethanol, sulfhydryl containing reducing agents, or dextran sulfate in the buffer significantly reduces the binding effect.

DETECTION OF BOUND PROBE MOLECULES

Currently, the most common technique for detecting the presence of probe molecules hybridized to the immobilized DNA is by detecting radioactive labels affixed to the probes. Such labels produce visible bands or dots when the hybridization membrane is subject to autoradiography. More specifically, the membrane is blotted partially dry and then affixed to a solid backing such as heavy paper or cardboard. Radioactive or fluorescent ink is used to define the edges and orientation of the membrane, and provide identification. The membrane is then placed in a holder with x-ray film, such as Kodak XOMAT-AR5, and allowed to expose the film for a few hours or days, depending upon the intensity of the radioactive signal. If $^{32}$P is used as the isotope, intensifying screens (such as the DuPont Quanta II) may be used to decrease the exposure time.

In practice, autoradiography will likely be the most common detection method used with the present invention. However, bound probe molecules can also be detected and their mass measured by liquid scintillation counting of membrane squares containing immobilized DNA and bound probe molecules. The actual mass of bound probe molecules can be calculated from the observed counts and the known specific activity of the probe molecules in dpm/ug.

Alternatively, if the probe molecules are tagged with a chemical modification such as a biotinylated nucleotide, the modification of bound probe molecules is detected in a known manner suited for the particular modification.

EXPERIMENTAL MATERIALS AND METHODS

The following examples are offered by way of illustration and not by way of limitation.

Isolation and Purification of DNA Samples

Plasmid DNA was isolated in a known manner. See, for example, Maniatis et al., *Molecular Cloning*, A Laboratory Manual, pp. 86-96 (published by Cold Spring Harbor). The specific techniques used in these experiments are described in Free, et al., *J. Bacteriol.* 137:1219-26 (1979).

Genomic DNA from *Neurospora crassa* was isolated and purified as described in Rodland and Russell, *Current Genetics* 7:379 (1983). Human genomic DNA was isolated from lymphocytes using the procedure of Gross-Ballard, *Europ. J. Biochem.* 36:32 (1973).

Preparation of DNA probes

DNA probes were labeled using the modifications of Rigby et al., *J. Mol. Biol.* 113:237 (1977) described in Rodland and Russell, *Biochim Biophys Acta* 697:162 (1982) and in accordance with the protocol earlier described. The same technique was used with each of $^{32}$P, $^{3}$H, or $^{35}$S as the radioactive label. Generally, a thionucleotide was incorporated into each of the experimental probes (as distinguished from the control probes). The control probes were incubated in the reaction mixture for 90 minutes, as taught by Rigby et al. However, whenever the thionucleotide deoxycytosine 5'αthio-triphosphate was incorporated into the probe, the reaction incubation was extended to 5-6 hours. The extended incubation was applied to both $^{32}$S and $^{35}$S.

If a cold ($^{32}$S) thionucleotide was incorporated, the DNA probe was simultaneously labeled with either deoxyadenosine 5'triphosphate-[α$^{32}$P] or deoxyadenosine 5'triphosphate-[2,8,5'$^{3}$H]. The concentration of each deoxynucleotide was kept at 15 μM, including the thionucleotides. Radioactively labeled deoxyadenosine 5'triphosphateα-[$^{32}$P] and -[$^{3}$H], deoxycytosine 5'triphosphate-[$^{32}$P] and deoxycytosine 5'αthio-triphosphateα-[$^{35}$S] used experimentally was obtained from New England Nuclear, Boston, Mass., as was the cold thionucleotide deoxycytosine 5'αthio-triphosphateα-[$^{32}$S]. Specific activities of $0.5-4.0\times10^7$ dpm/ug were consistently obtained, regardless of the isotope used.

Immobilization of DNA

For most of the initial experiments, the total DNA sample was immobilized on hybridization membranes using a modified "dot blot" method, without previous enzymatic digestion or size separation. By way of explanation, the general procedure for "dot-blotting" was first described by Kafatos et al., *Nucleic Acid Res.*

7:1541 (1979) for use with nitrocellulose membranes. However, the actual procedure followed was modified for use with nylon membranes as indicated below.

The DNA sample was initially denatured by a 10 minute incubation at room temperature in 0.5N NaOH. Subsequently, a tenfold excess of ice cold 0.12M sodium phosphate buffer, pH 6.5, was added and the resulting mixture immediately placed on ice to prevent re-annealing of the strands.

The nylon membranes were pre-wet in distilled water and placed on a supporting piece of chromatography paper. The paper was then placed in a "dot-blotting manifold" (BRL's "Hybri-Dot" or Schleicher & Schuell's "Mini-Fold I"). Wells of the manifold were loaded with the DNA sample. Enough DNA sample to provide 1–10 µg per well, and enough of the 0.12M sodium phosphate buffer to provide a loading volume of 100 µl per well were added. An automatic pipettor (such as the "FinnPipette" or "Gilson Pipetteman") was used to load 100 µl of this mixture into each well. The loading was accomplished by gravity filtration for one hour or less. Each well was then washed with 300 µl of the cold phosphate loading buffer, applied under gentle suction. The hybridization membrane containing the DNA samples was removed from the apparatus, air dried, and then handled in a known manner. Although a DNA sample size of 1–10 µg is preferred, sample sizes outside this range can be used.

In two of the experiments, the DNA sample was digested with restriction endonucleases and the resulting fragments separated in agarose gels in a known manner, i.e., as taught by Sourthern, supra. The size-separated DNA fragments were then transferred to the hybridization membranes by either capillary transfer or electrophoretic transfer in accordance with the protocols earlier described. See also, Rodland and Russell, *Biochim Biophys Acta* 697: 162 (1982); *Current Genet.* 7: 379 (1983). Nylon memberanes were air dried following the transfer, while nitrocellulose membranes were heated in a vacuum oven at 80° C. for 2 hours.

Hybridization of DNA Immobilized on Membranes

For hybridization purposes, all nylon and nitrocellulose membranes were treated in the same manner. The membranes were pre-hybridized by incubation at 65° C. in a buffer having 5X SSPE (0.75M NaCl, 75 mM sodium phosphate pH 6.5, 5 nM EDTA) and 0.1 sodium dodecyl sulfonate for 12–24 hours. They were pre-hybridized in heat-sealed plastic bags (i.e., Sears "Seal-a-Meal"), with a small volume of buffer, generally 1 ml per 50–100 cm$^2$ of membrane.

Thereafter, the probe DNA and any desired experimental additives were added directly to the unsealed bag. In these experiments, less than 1/10 volume of the additive would be added. The probe volumes were 30–75 µl, containing 1–3×10$^6$ cpm (100–500 ng) DNA. The probe solution was gently mixed with the pre-hybridization solution. All air bubbles were expelled, and the bag was re-sealed. No measureable quantities of any nonpolar solvents such as formamide, reducing agents such as dithiothreitol and 2-mercaptoethanol, or dextran sulfate were present in the solution, except where added to test the effect of the same. The hybridization mixture was incubated for 4–30 hours, usually about 20 hours, at 65° C. with constant agitation. Nonspecifically bound probe molecules were removed by washing the membranes according to the procedure described by Jeffreys and Flavell, *Cell* 12: 429 (1977). The protocol just outlined follows the hybridization protocol earlier described.

Detection and Quantification of Bound Probe Molecules

After the hybridization and washing steps, the membranes were used to expose X-ray film according to standard autoradiographic procedures to qualitatively measure the relative binding of the experimental and control probes. See, for example, Maniatis et al. manual, supra. The actual amount of probe bound determined by liquid scintillation counting of membrane squares containing 3 or 4 "dots" of DNA, which had been treated in identical fashion. These squares were dried, placed in scintillation vials, and submerged with scintillation cocktail (i.e., "Aquasol" by New England Nuclear), to render the membranes translucent. Quenching was determined not to be a significant variable. A known sample of DNA probe solution was spotted onto a membrane and counted under the same conditions to determine the specific activity of the DNA probe. The mass of DNA probe bound to the membranes was then calculated from the observed cpm, quench data, and calculated specific activity of the probe in a known manner.

TABLE I

| | Relative Hybridization of DNA Probes Constructed With and Without Thionucleotides | | | | |
|---|---|---|---|---|---|
| Immobilized DNA | Experimental Probe | Ng of Bound Experimental Probe Containing Thionucleotides | Control Probe | Ng of Bound Control Probe | Binding Ratio DNAα$^S$/DNA |
| pKD002 | pKD002α[$^{35}$S] | 24.2 ± 1.55 | pKD002-[$^{32}$P] | 0.198 ± 0.002 | 120 |
| pKD002 | pkD002α[$^{35}$S] | 29.42 ± 0.21 | pKD002-[$^{32}$P] | 0.70 ± 0.15 | 42 |
| pKD002 | pKD002α[$^{35}$S] | 25.2 ± 8.9 | pKD002-[$^{32}$P] | 1.63 ± 0.66 | 15 |
| pKD003 | pKD003α[$^{35}$S] | 16.07 ± 0.31 | pKD003-[$^{32}$P] | 0.399 ± 0.18 | 40 |
| pKD003 | pKD003α[$^{35}$S] | 52.99 ± 3.12 | pKD003-[$^{32}$P] | 1.176 ± 0.234 | 45 |

EXAMPLE 1

Comparison of $^{32}$P-labeled and $^{35}$S-labeled DNA probes

Table I shows the results of several separate experiments in which probe molecule pairs, one constructed to contain deoxycytosine 5'triphosphateα-[$^{32}$P] and the other to contain deoxycytosine 5'αthiotriphosphate-[α$^{35}$S], were compared directly. In these experiments, 0.5 to 1.0 µg of DNA from the recombinant plasmid pKD002 (containing genes for rRNA from *Neurospora crassa* inserted in the plasmid pBR322) was immobilized on a "GeneScreen" membrane by dot-blotting. The membranes were hybridized in 5X SSPE, 0.1% SDS, at 65° C. for 24 hours. The bound DNA was measured by liquid scintillation counting. In these experiments, the mass of $^{35}$S-labeled probe bound exceeded that of the $^{32}$P-labeled probe by a factor of 15 to 120.

Part B, human genomic DNA was immobilized by dot-blotting (1 μg per dot), and probed with labeled DNA from the plasmid pJW103, which contains coding se-

TABLE II

Relative Hybridization of DNA Probes Constructed With and Without Thionucleotides

| Immobilized DNA | Experimental Probe | Ng of Bound Experimental Probe Containing Thionucleotides | Control Probe | Ng of Bound Control Probe | Binding Ratio DNAα$^S$/DNA |
|---|---|---|---|---|---|
| Part A | | | | | |
| pKD003 | pKD003α$^{32}$S-[$^{32}$P] | 8.76 ± 0.43 | pKD003-[$^{32}$P] | 4.71 ± 0.93 | 1.86 |
| pKD003 | pKD003α$^{32}$S-[$^{32}$P] | 9.34 ± 1.36 | pKD003-[$^{32}$P] | 5.00 ± 0.22 | 1.87 |
| pKD003 | pKD003α$^{32}$S-[$^{32}$P] | 11.20 ± 0.55 | pKD003-[$^{32}$P] | 4.55 ± 0.15 | 2.46 |
| pKD003 | pKD003α$^{32}$S-[$^3$H] | 5.15 ± 0.10 | pKD003-[$^3$H] | 2.59 ± 0.11 | 1.99 |
| pKD003 | pKD003α$^{32}$S-[$^3$H] | 0.635 ± 0.114 | pKD003-[$^3$H] | 0.127 ± 0.049 | 5.0 |
| Part B | | | | | |
| human genomic DNA | pJW103α$^{32}$S-[$^{32}$P] human β-globin | 0.16 ± 0.020 | pJW103-[$^{32}$P] human β-globin | 0.04 ± 0.004 | 4.0 |
| human genomic DNA | pJW103α$^{32}$S-[$^{32}$P] human β-globin | 0.17 ± 0.012 | pJW103-[$^{32}$P] human β-globin | 0.02 ± 0.004 | 8.5 |

EXAMPLE 2

Effect of Cold Thionucleotides on Probe Binding

Another set of experiments, summarized in Table II, Part A, were conducted using the same protocol as Example 1, except that the non-radioactive thionucleotide deoxycytosine 5'αthiotriphosphateα-[$^{32}$S] was incorporated into DNA probes labeled with either $^{32}$P (deoxyadenosine 5'triphosphate-[α$^{32}$P]) or $^3$H (deoxyadenosine 5'triphosphate-[2,8,5' $^3$H]). As with Example 1, such probes were compared to conventional control probes lacking thionucleotides. In these experiments, the incorporation of cold thionucleotides increased the mass of probe bound by a factor of about 2 to 5. These experiments neutralized any difference in radiolysis between $^{35}$S and $^{32}$P (due to the higher decay energy of the latter) as the sole cause of the increased binding phenomena in Example 1. This series of experiments demonstrated that the increased binding effect is specific to the inclusion of a thionucleotide, and independent of the radioisotope used to label the DNA molecule.

EXAMPLE 3

Amplification of Probe Binding When Genomic DNA is Used

The observation that a probe containing thionucleotides increases the amount of probe hybridized to immobilized DNA, and therefore the detectable signal, is particularly significant if the effect can be used to increase the sensitivity for detecting single copy genes in human DNA. In two experiments, shown in Table II, quences for the human gamma globin gene. See Wilson et al., *Nucleic Acids Research* 5: 563–81 (1978). The gamma globin gene of both the experimental and control probes are labeled with $^{32}$P as deoxyadenosine 5' triphosphate[$^{32}$P]. The control probes further incorporated deoxycytosine 5'triphosphate while the experimental probes incorporated deoxycytosine 5'αthiotriphosphate[α$^{32}$S] (the non-radioactive isotope of sulfur). In the absence of thionucleotides, a weighted average of 0.03±0.004 ng of pJW103 was bound, compared to a weighted average of 0.165±0.016 ng of pJW103 containing the thionucleotide. This represents an amplification factor of 5.5.

In a similar experiment, 4 μg per dot of genomic *Neurospora crassa* DNA was immobilized by dot-blotting and probed with recombinant plasmid pKD003, which contains part of the gene coding for rRNA in *Neurospora crassa*, inserted into the bacterial plasmid pBR322. Both "GeneScreen" and "GeneScreen Plus" membranes were used to immobilize the DNA. These membranes were then hybridized as previously described, and the mass of probe bound measured. These calculations showed that 2.12±0.08 ng of thionucleotide-containing probe pKD003α[$^{35}$S] had bound to the DNA immobilized on GeneScreen, compared to 0.024±0.002 ng of control probe pKD003-[$^{32}$P], for a ratio of 88 to 1. A similar effect was observed on GeneScreen Plus: 8.90±0.78 ng of thionucleotide containing probe (pKD003α[$^{35}$S]) bound compared to 0.069±0.004 ng of control probe (pKD003-[$^{32}$P]), for a ratio of 129 to 1.

TABLE III

Effect of Different Membranes on Relative Hybridization of Lambda DNA Probes Constructed With and Without Thionucleotides

| Membrane | Experimental Probe | Ng of Bound Experimental Probe Containing Thionucleotides | Control Probe | Ng of Bound Control Probe | Binding Ratio DNAα$^S$/DNA |
|---|---|---|---|---|---|
| GeneScreen | HindIII cut λα[$^{35}$S]-[$^{32}$P] | 12.36 | Hind III cut λ-[$^{32}$P] | 0.68 | 18 |
| GeneScreen Plus | HindIII cut λα[$^{35}$S]-[$^{32}$P] | 33.49 | Hind III cut λ-[$^{32}$P] | 1.94 | 17 |
| Zeta-Probe | HindIII cut λα[$^{35}$S]-[$^{32}$P] | 55.87 | Hind III cut λ-[$^{32}$P] | 2.22 | 25 |
| Pall-Biodyne | HindIII cut λα[$^{35}$S]-[$^{32}$P] | 9.15 | Hind III cut λ-[$^{32}$P] | 0.74 | 12 |
| Nitrocellulose | HindIII cut | 0.86 | Hind III cut λ-[$^{32}$P] | 0.32 | 2.7 |

TABLE III-continued

Effect of Different Membranes on Relative Hybridization of Lambda DNA Probes Constructed With and Without Thionucleotides

| Membrane | Experimental Probe | Ng of Bound Experimental Probe Containing Thionucleotides | Control Probe | Ng of Bound Control Probe | Binding Ratio DNA$\alpha^S$/DNA |
|---|---|---|---|---|---|
| | $\lambda\alpha[^{35}S]\text{-}[^{32}P]$ | | | | |

EXAMPLE 4

Comparison of Hybridization Membranes

In order to determine the generality of the observed amplification of probe binding, various commerically available hybridization membranes were tested. Bacteriophage lambda DNA previously digested with the restriction enzyme HindIII (obtained from Bethesda Research Laboratories, Gaithersburg, Md.) was fractionated by electrophoresis on agarose gels and transferred to various membranes by capillary wicking. Five identical lanes were used, with 3 μg of DNA in each lane, and each lane was covered with a different membrane strip, namely "GeneScreen" (nylon), "GeneScreen Plus" (nylon), both from New England Nuclear, "Zeta-Probe" (nylon) from BioRad, Richmond, Ca., Membrane A (nylon) from Pall Biodyne and nitrocellulose (Bethesda Research Laboratories, Gaithersburg, Md.). These membranes were treated as described in the "Materials and Methods" section and then hybridized with identical HindIII digested lambda DNA which incorporated either deoxycytosine 5'triphosphate-$[^{32}P]$ alone, or deoxycytosine 5'triphosphate-$[^{32}P]$ plus deoxyadenosine 5'$\alpha$thio-triphosphate$\alpha$-$[^{35}S]$. Hybridization was conducted as before, with the mass of bound lambda DNA being calculated from the observed cpm in the high energy $^{32}P$ channel (the $^{35}S$ emissions are less energetic and do not contribute at all to counts measured at this energy level). Table III shows the results of this experiment. In all the membranes tested, incorporation of thionucleotides increased the mass of lambda DNA bound in comparison to the conventional control probe. However, the effect is far more striking for nylon than nitrocellulose membranes.

EXAMPLE 5

Effect of Reducing Agents

Experiments were performed in which a reducing agent (specifically either dithiothreitol or 2-mercaptoethanol) was added to the hybridization buffer. In all other respects the protocol followed was identical to that described in Examples 1 and 2. The results of these experiments are summarized in Table IV. The presence of either dithiothreitol or 2-mercaptoethanol in the hybridization buffer reduced the amount of bound probe. It has been observed that the amplification effect can be completely abolished at very high concentrations of reducing agent.

EXAMPLE 6

Effect of Formamide

The hybridization protocol described in Examples 1 and 2 is one of at least two commonly used procedures for nucleic acid hybridization reactions. In an alternative procedure, formamide (up to 50% by volume) is added to the hybridization buffer to lower the melting temperature of the DNA helix, thereby allowing the re-annealing process to occur at a lower incubation temperature.

The addition of formamide (50% by volume) to the hybridization buffer described in Example 1 eliminates the amplification effect otherwise present when cold thionucleotides are incorporated into the probe molecule. In one experiment, the amount of probe DNA bound was compared for probes incorporating either $^{32}P$-deoxyadenosine alone or $^{32}P$-deoxycytosine plus deoxycytosine $\alpha$-thio-triphosphate$[^{32}S]$, with and without 50% formamide in the hybridization buffer. In the absence of formamide, about twice as much experimental probe (containing $^{32}S$) as control probe (24 ng vs 12 ng) bound. When formamide was present in the buffer, the amounts of bound probe were nearly identical, 14.3 ng of experimental probe as compared to 13.6 ng of control probe.

TABLE IV

Effect of Reducing Agent on Increased Binding

| Experimental Probe | Reducing Agent | Ng of Bound Experimental Probe Hybridized in Absence of Reducing Agent | Ng of Bound Experimental Probe Hybridized in Buffer Containing Reducing Agent | Control Probe | Ng of Bound Control Probe Hybridized in Absence of Reducing Agent | Ratio of Experimental Probe Binding Plus/Minus Reducing Agent |
|---|---|---|---|---|---|---|
| pKD003$\alpha[^{35}S]$ | dithiothreitol (10 mM) | 6.95 ± 0.88 | 5.03 ± 0.88 | — | — | 0.72 |
| pKD003$\alpha[^{35}S]$ | dithiothreitol (10 mM) | 0.367 ± 0.104 | 0.147 ± 0.010 | — | — | 0.40 |
| pKD003$\alpha[^{35}S]$ | dithiothreitol (10 mM) | 0.96 ± 0.213 | 0.344 ± 0.036 | — | — | 0.36 |
| pKD003$\alpha[^{35}S]$ | dithiothreitol (10 mM) | 0.57 ± 0.06 | 0.36 ± 0.64 | — | — | 0.63 |
| pKD003$\alpha^{32}$S-$[^{32}P]$ | dithiothreitol (10 mM) | 8.76 ± 0.86 | 6.89 ± 0.98 | pKD003-$[^{32}P]$ | 4.71 ± 1.86 | 0.79 |
| pKD003$\alpha^{32}$S-$[^{3}H]$ | dithiothreitol (10 mM) | 1.010 ± 0.114 | 0.523 ± 0.014 | pKD003-$[^{3}H]$ | 0.668 ± 0.42 | 0.52 |
| pKD003$\alpha^{32}$S-$[^{32}P]$ | dithiothreitol (10 mM) | 9.34 ± 2.72 | 4.43 ± 1.74 | pKD003-$[^{3}H]$ | 5.00 ± 0.44 | 0.47 |
| pKD003$\alpha[^{35}S]$ | dithiothreitol (10 mM) | 3.13 ± 0.28 | 1.94 ± 0.90 | — | — | 0.62 |
| pKD003$\alpha^{32}$S-$[^{32}P]$ | dithiothreitol (10 mM) | 11.20 ± 1.10 | 7.61 ± 0.60 | pKD003-$[^{32}P]$ | 4.55 ± 0.30 | 0.68 |
| pMF2$\alpha^{32}$S-$[^{32}P]$ | 1% 2-mercaptoethanol | 62.6 ± 8.4 | 54.8 ± 4.2 | pMF2-$[^{32}P]$ | 19.1 ± 2.7 | 0.88 |

THEORETICAL BASIS OF THE INVENTION

This section attempts to provide a few theoretical bases for the increased binding phenomenon associated with the invention. While the precise chemical mechanism which causes the observed increase in probe binding is not yet thoroughly understood, enough data has been accumulated to permit generalizations about those factors which might contribute to the phenomenon.

It is clear from the combined data of Tables I and II that the inclusion of thionucleotides into DNA probe molecules consistently increases the amount of probe subsequently hybridized to immobilized DNA. The increased binding is specific for complementary sequences, and is observed with the incorporation of either radioactive or stable isotopes of sulfur into the probe.

Looking at Table I alone, it might be theorized that the increased binding phenomenon is caused by a radioisotopic effect. Since $^{32}P$ has a higher emission energy than does $^{35}S$, disintegration of $^{32}P$ during radioactive decay is more likely to produce significant radiolytic degradation of the DNA polymer than disintegration of $^{35}S$. A comparison of the amplification ratios obtained when DNA is labeled with $^{35}S$ versus the non-radioactive isotope $^{32}S$ shows that decreased radiolysis does contribute substantially to increased probe binding. However, the incorporation of non-radioactive thionucleotides still produces a significant increase in the amount of probe hybridized (Table II), and therefore decreased radiolysis alone is an insufficient explanation.

Two possible explanations for the increased binding phenomenom are supported by the data presented. The first explanation is based upon the known ability of sulfhydryl compounds (—SH) to form covalent disulfide bonds with each other following the loss of two protons [e.g. $R_1$—SH+HS—$R_2$ goes to $R_1$—S—S—$R_2$]. Given the possible resonance forms of the phosphothiodiester bond in the DNA polymer, it would be theoretically possible for such disulfide bonds to form between individual DNA polymers containing thionucleotides. If one member of the linked pair of thionucleotides formed Watson-Crick base pairs with the complementary strand of immobilized DNA, the additional strand(s) linked by disulfide bonds would contribute to the mass of bound probe, and to the hybridization signal. This hypothesis is supported by the observation that the addition to the hybridization buffer of dithiothreitol (Cleland's reagent), a compound known to inhibit the formation of disulfide bonds between other sulfhydryl-containing molecules, decreases or negates altogether the increased binding phenomenon. It is also supported by the negative effect which 2-mercaptoethanol has on the phenomenon.

The second explanation relates to the degree to which the membrane-immobilized nucleic acid samples are accessible to the DNA probe molecules. The "accessibility" factor has a significant effect on the amount of probe binding which occurs. The probe molecules must come into close proximity with the immobilized DNA molecule before the requisite hydrogen bonds can form. Various physical characteristics of the hybridization membrane, such as but not limited to pore size, surface charge, and hydrophobicity, are known to affect the binding of macromolecules to the membranes. Since the incorporation of thionucleotides into the probe molecule changes several physical characteristics of the molecule (e.g. decreasing the electronegativity and charge density of the molecule), it is possible that these physical changes may increase the ability of the probe molecule to penetrate the membrane and interact with the immobilized DNA molecule. However, it is not clear how the inclusion of thionucleotides would affect this process, since the precise physical nature of DNA binding to nitrocellulose and/or nylon membranes is poorly understood. In any event, the data consistently shows the existence of such effect. For example, the magnitude of the observed amplification appears to be membrane-dependent, with nylon membranes seemingly interacting synergistically with the thionucleotides to maximize the increase in probe binding.

Furthermore, the addition of formamide has a negative effect on the observed amplification, eliminating it altogether at high concentrations. Formamide is a less polar solvent than water, and reduces the melting temperature of the DNA duplex, facilitating the re-annealing process. The non-polar nature of formamide may interfere with the interactions between the thionucleotides and the immobilizing membrane to decrease binding.

Dextran sulfate is also exluded from the hybridization buffer because it negatively affects the increased binding phenomenon. Dextran sulfate contains a sulfate group which could be reacting with the tiol group of the thionucleotide, thereby interfering with the chemical reaction or interaction responsible for the increased binding.

These are only the most likely explanations of the phenomenon, based on currently available data. The role of other factors or mechanisms in this process may become evident as more basic research is done on the chemical mechanisms of membrane hybridization reactions.

Although the foregoing invention has been described in some detail by way of illustration and example for purposes of clarity of understanding, it is obvious that certain changes and modifications may be practiced within the scope of the appended claims.

What is claimed is:

1. A method for detecting the presence of a nucleotide sequence in substantially single stranded form in a sample suspected of containing said sequence, said method comprising:

annealing to said nucleotide sequence, a probe that is complementary to said suspected sequence and contains both a detectable label other than $^{35}S$ and a thionucleotide in which the thiol group is nonradioactive; and detecting the presence of the labeled probe annealed to said nucleotide sequence.

2. A method according to claim 1 wherein said nonradioactive thionucleotide is either deoxycytosine 5'αthio-triphosphateα-[$^{32}S$] or deoxyadenosine 5'αthio-triphosphateα-[$^{32}S$].

3. A method according to claim 2 wherein said probe has a radioactive isotope as a label.

4. A method according to claim 3 wherein said radioactive isotope is one of $^3H$, $^{14}C$, $^{32}P$, or $I^{125}$.

5. A method according to claim 2 wherein said probe is labeled with both a radioactive isotope and a detectable chemical modification.

6. A method according to claim 5 wherein said chemical modification is a biotinylated nucleotide and said radioactive isotope is one of $^3H$, $^{14}C$, $^{32}P$, or $I^{125}$.

7. A method according to claim 2 wherein said probe is labeled with a detectable chemical modification.

8. A method according to claim 2 wherein said nucleotide sequence is immobilized on a membrane before being annealed to said probe.

9. A method according to claim 8 wherein said membrane is a nylon base membrane.

10. A method according to claim 8 wherein said membrane has a pore size greater than 0.45 microns.

11. A method according to claim 8 wherein said probe and nucleotide sequence are annealed in the absence of a nonpolar solvent.

12. A method according to claim 11 wherein the annealing occurs in the absence of formamide.

13. A method according to claim 8 wherein said probe and nucleotide sequence are annealed in the absence of a reducing agent.

14. A method according to claim 8 wherein said probe and nucleotide sequence are annealed in the absence of a sulfhydryl containing reducing agent.

15. A method according to claim 14 wherein said annealing occurs in the absence of either dithiothreitol or 2-mercaptoethanol.

16. A method according to claim 8 wherein said probe and nucleotide sequence are annealed in the absence of dextran sulfate.

17. A method according to claim 8 wherein said probe and nucleotide sequence are annealed in the absence of a nonpolar solvent, reducing agent and dextran sulfate.

18. A method according to claim 17 wherein said annealing occurs in the absence of dextran sulfate, formamide and dithiothreitol.

19. A method according to claim 2 wherein said nucleotide sequence is genomic DNA from *Neurospora crassa*.

20. A method according to claim 2 wherein said nucleotide sequence is human genomic DNA.

21. A method according to claim 2 wherein said nucleotide sequence is plasmid DNA.

22. A method of constructing a probe for hybridizing to a nucleotide sequence of interest comprising:
  selecting a nucleic acid polymer complementary to said nucleotide sequence;
  substituting at least one thionucleotide having a non-radioactive thiol group for an analogous nucleotide present in said polymer; and
  labeling said polymer with a detectable label other than $^{35}S$.

23. A method according to claim 22 wherein said non-radioactive nucleotide is either deoxycytosine 5'αthio-triphosphateα-[$^{32}S$] or deoxyadenosine 5'αthio-triphosphateα-[$^{32}S$].

24. A method according to claim 23 wherein said label is a radioactive isotope.

25. A method according to claim 24 wherein said radioactive isotope is one of $^{3}H$, $^{14}C$, $^{32}P$, or $^{125}I$.

26. A method according to claim 22 wherein said label is a detectable chemical modification.

27. A method according to claim 22 wherein said probe is labeled with both a radioactive isotope and detectable chemical modification.

28. A hybridization probe of the formula

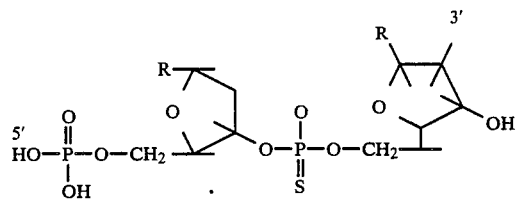

wherein R is any purine or pyrimidine base, S is $^{32}S$, and the probe has incorporated a radioactive isotope other than $^{35}S$.

29. A probe according to claim 28 wherein said radioactive isotope is one of $^{3}H$ substituting for any H, $^{14}C$ substituting for any C, $^{32}P$ substituting for any P, or $^{125}I$ present in any iodinated modification in a purine or pyrimidine base.

30. A probe according to claim 28 wherein said purine or pyrimidine bases contains a detectable chemical modification.

31. A hybridization probe of the formula

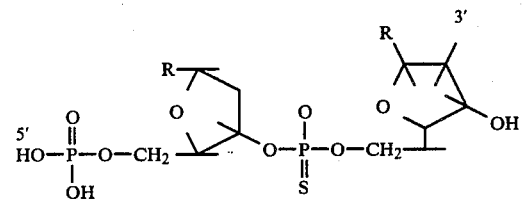

wherein R is any purine or pyrimidine base containing a detectable chemical modification and S is $^{32}S$.

32. A method for detecting the presence of a nucleotide sequence in substantially single stranded DNA form in a sample suspected of containing said sequence, said method comprising:
  forming a labeled DNA probe that is complementary to said suspected sequence and contains a thionucleotide attached to a phosphate base of said probe;
  annealing said nucleotide sequence in the absence of a nonpolar solvent, reducing agent and dextran sulfate to said labeled probe; and
  detecting the presence of the labeled probe annealed to said nucleotide sequence.

33. A method according to claim 32 wherein the annealing occurs in the absence of a sulfhydryl-containing reducing agent and formamide 34. A method according to claim 33 wherein the annealing occurs in the absence of both dithiothreitol and 2-mercaptoethanol.

35. A method for detecting the presence of a nucleotide sequence in substantially single stranded form in a sample suspected of containing said sequence, said method comprising:
  annealing to said nucleotide sequence, a probe that is complementary to said suspected sequence and contains an incorporated thionucleotide and an incorporated detectable label other than $^{35}S$ in addition to said thionucleotide; and
  detecting the presence of the probe annealed to said nucleotide sequence by detecting the signal generated by said label.

36. A method according to claim 35 wherein said label is a radioactive isotope.

37. A method according to claim 36 wherein said radioactive isotope is one of $^{3}H$, $^{14}C$, $^{32}P$, or $^{125}I$.

38. A method according to claim 35 wherein said label is a chemical modification.

39. A method according to claim 38 wherein said chemical modification is a biotinylated nucleotide.

40. A method of constructing a probe for hybridizing to a nucleotide sequence of interest comprising:
  selecting a nucleic acid polymer complementary to said nucleotide sequence;
  substituting at least one thionucleotide for an analogous nucleotide present in said polymer; and labeling said polymer with a detectable label other than $^{35}S$ in addition to said thionucleotide.

41. A method according to claim 40 wherein said label is a radioactive isotope.

42. A method of claim 40 wherein said label is a chemical modification.

43. A hybridization probe of the formula

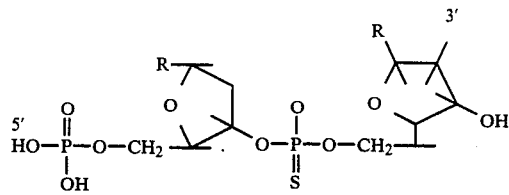

wherein R is any purine or pyrimidine base, S is $^{35}S$ or $^{32}S$, and the probe has incorporated a radioactive isotope other than $^{35}S$.

44. A hybridization probe of the formula

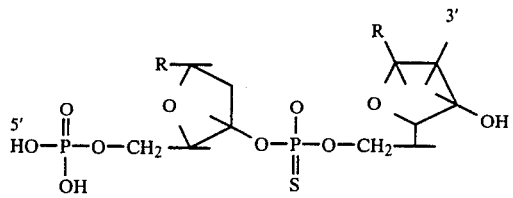

wherein R is any purine or pyrimidine base containing a detectable chemical modification and S is $^{32}S$ or $^{35}S$.

45. A method of constructing a probe for hybridizing to a nucleotide sequence of interest comprising:
  selecting a nucleic acid polymer complementary to said nucleotide sequence;
  substituting at least one thionucleotide having a non-radioactive thiol group for an analogous nucleotide present in said polymer; and
  labeling said polymer with a detectable label.

* * * * *

UNITED STATES PATENT AND TRADEMARK OFFICE
CERTIFICATE OF CORRECTION

PATENT NO. : 4,647,529

DATED : March 3, 1987

INVENTOR(S) : KARIN D. RODLAND, PETER J. RUSSELL

It is certified that error appears in the above-identified patent and that said Letters Patent is hereby corrected as shown below:

In the Specification:

Column 5, lines 10-20 replace the molecule shown with the following molecule:

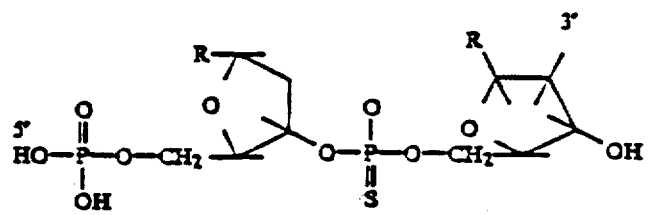

Column 6, lines 13-27 replace the molecule shown with the following molecule:

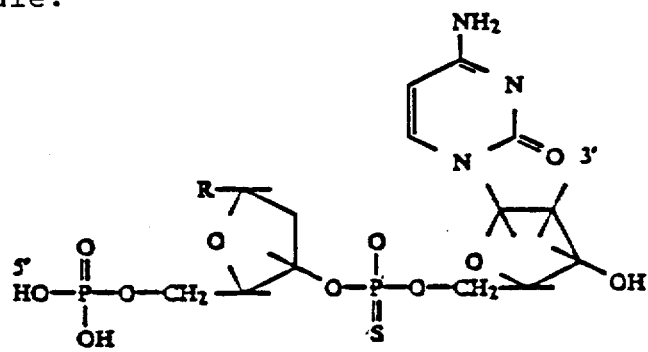

UNITED STATES PATENT AND TRADEMARK OFFICE
CERTIFICATE OF CORRECTION

PATENT NO. : 4,647,529

DATED : March 3, 1987

INVENTOR(S) : KARIN D. RODLAND, PETER J. RUSSELL

It is certified that error appears in the above-identified patent and that said Letters Patent is hereby corrected as shown below:

In the Claims:

Claim 28, column 19, lines 59-68 replace the molecule shown with the following molecule:

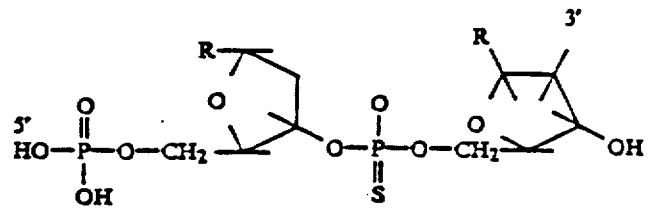

Claim 31, column 20, lines 13-22 replace the molecule shown with the following molecule:

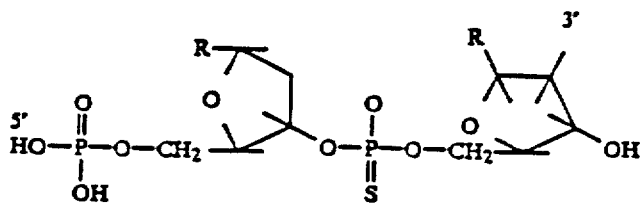

UNITED STATES PATENT AND TRADEMARK OFFICE
CERTIFICATE OF CORRECTION

PATENT NO. : 4,647,529

DATED : March 3, 1987

INVENTOR(S) : KARIN D. RODLAND, PETER J. RUSSELL

It is certified that error appears in the above-identified patent and that said Letters Patent is hereby corrected as shown below:

In the Claims (cont.):

Claim 43, column 21, lines 8-17 replace the molecule shown with the following molecule:

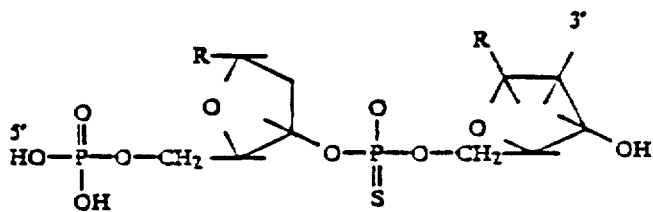

UNITED STATES PATENT AND TRADEMARK OFFICE
CERTIFICATE OF CORRECTION

PATENT NO. : 4,647,529
DATED : March 3, 1987
INVENTOR(S) : KARIN D. RODLAND, PETER J. RUSSELL It is certified that error appears in the above-identified patent and that said Letters Patent is hereby corrected as shown below:

In the Claims (cont.):

Claim 44, column 22, lines 1-9 replace the molecule shown with the following molecule:

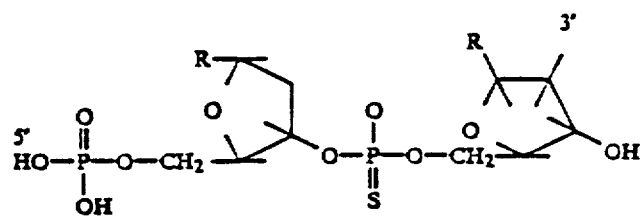

Signed and Sealed this

Second Day of February, 1988

Attest:

DONALD J. QUIGG

Attesting Officer      Commissioner of Patents and Trademarks